(12) United States Patent
Fong et al.

(10) Patent No.: US 8,318,420 B2
(45) Date of Patent: Nov. 27, 2012

(54) HEATED ASSAYS FOR INFLUENZA

(75) Inventors: Whalley K. Fong, Coquitlam (CA); Paul C. Harris, Bothell, WA (US)

(73) Assignee: Response Biomedical Corporation, Vancouver (CA)

( * ) Notice: Subject to any disclaimer, the term of this patent is extended or adjusted under 35 U.S.C. 154(b) by 111 days.

(21) Appl. No.: 12/834,116

(22) Filed: Jul. 12, 2010

(65) Prior Publication Data
US 2011/0269115 A1 Nov. 3, 2011

Related U.S. Application Data

(63) Continuation of application No. PCT/US2009/000035, filed on Jan. 6, 2009.

(60) Provisional application No. 61/011,593, filed on Jan. 18, 2008.

(51) Int. Cl.
*C12Q 1/70* (2006.01)
*G01N 33/569* (2006.01)

(52) U.S. Cl. .......................... 435/5; 436/501

(58) Field of Classification Search .................. None
See application file for complete search history.

(56) References Cited

U.S. PATENT DOCUMENTS

| | | |
|---|---|---|
| 5,652,093 A | 7/1997 | Cubbage et al. |
| 5,888,733 A | 3/1999 | Hyldig-Nielsen et al. |
| 5,939,252 A * | 8/1999 | Lennon et al. .................. 435/4 |
| 7,595,152 B2 * | 9/2009 | Lu et al. .......................... 435/5 |
| 2002/0127547 A1 | 9/2002 | Miller |
| 2004/0202996 A1 | 10/2004 | Williams et al. |
| 2011/0269115 A1 * | 11/2011 | Fong et al. .................. 435/5 |

FOREIGN PATENT DOCUMENTS

| | | |
|---|---|---|
| EP | 1 167 382 A1 | 1/2002 |
| EP | 1 826 269 A1 | 8/2007 |
| WO | WO 95/02699 A1 | 1/1995 |
| WO | WO 2007/095155 A2 | 8/2007 |
| WO | WO 2009/091501 A1 | 7/2009 |

OTHER PUBLICATIONS

International Preliminary Report on Patentability completed Dec. 10, 2009, International Application No. PCT/US2009/000035, International Filing Date: Jan. 6, 2009.
International Search Report and Written Opinion of the International Searching Authority, International Application No. PCT/US2009/000035, International Filing Date: Jan. 6, 2009.

* cited by examiner

*Primary Examiner* — Shanon A Foley
(74) *Attorney, Agent, or Firm* — Jun He Law Offices P.C.; James J. Zhu

(57) ABSTRACT

Methods of increasing specific binding, decreasing non-specific binding, and reducing false-positive interaction in solid phase assays for influenza are disclosed. In the methods, the solid phase apparatus (lateral flow solid phase apparatus or capillary flow solid phase apparatus) is subjected to elevated heat subsequent to application of a test sample to the solid phase apparatus.

16 Claims, 7 Drawing Sheets

HEATED ASSAYS FOR INFLUENZA

RELATED APPLICATIONS

This application is a continuation of International Application No. PCT/US2009/000035, which designated the United States and was filed on Jan. 6, 2009, published in English, which claims the benefit of U.S. Provisional Application No. 61/011,593, filed on Jan. 18, 2008. The entire teachings of the above applications are incorporated herein by reference.

BACKGROUND OF THE INVENTION

Quantitative analysis of analytes in fluid samples, particularly bodily fluid samples, often provides critical diagnostic and treatment information for physicians and patients. In solid phase lateral flow and capillary flow assays, certain reagents are attached to a solid surface, facilitating separation of analytes. The solid phase is exposed to a sample containing the analyte; the extent of this binding is quantitated to provide a measure of the analyte concentration in the sample. Transduction of the binding event into a measurable signal, however, is affected by a number of limitations, including constraints of particle movement on the solid phase, which affect the specificity and applicability of quantitative assays. In addition, related analytes may compete with one another in an assay, rendering it difficult to assess correctly the presence of an analyte of interest.

SUMMARY OF THE INVENTION

The present invention is drawn to methods for decreasing non-specific binding of influenza detection particles, increasing specific binding of influenza detection particles, and/or reducing false-positive interaction of influenza detection particles, on a solid phase apparatus in an assay for one or more types of influenza of interest (e.g., influenza A, B, C). In the methods, a solid phase apparatus (a lateral flow solid phase apparatus or a capillary flow solid phase apparatus) and influenza detection particles are used. The influenza detection particles are coated with an agent that binds to a type of influenza of interest (e.g., antibody to the influenza of interest). The solid phase apparatus comprises an application point and at least one sample capture zone having a sample capture reagent immobilized thereon; the sample capture reagent comprises an agent that specifically binds to the type of influenza of interest (e.g., antibody to the influenza of interest).

In certain embodiments, the influenza detection particles are positioned at the application point of the solid phase apparatus; in other embodiments, the test sample comprises the influenza detection particles. In either embodiment, the test sample is applied to the solid phase apparatus, and the solid phase apparatus is then subjected to elevated temperatures. Elevated temperature can be about 5 to 20 degrees Celsius above ambient temperature, and is preferably between about 35 and 40 degrees Celsius, inclusive.

Application of the test sample to the solid phase apparatus results in movement of the influenza detection particles through the solid phase apparatus by capillary action. The influenza detection particles move to and through the sample capture zone, and may bind to the sample capture reagent. Subjecting the solid phase apparatus to elevated temperature results in a decrease of non-specific binding of influenza detection particles, an increase of specific binding of influenza detection particles, and/or a reduction of false-positive interaction of influenza detection particles in the sample capture zone of the solid phase apparatus. The methods thereby enhance the sensitivity and specificity of the assays for influenza.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
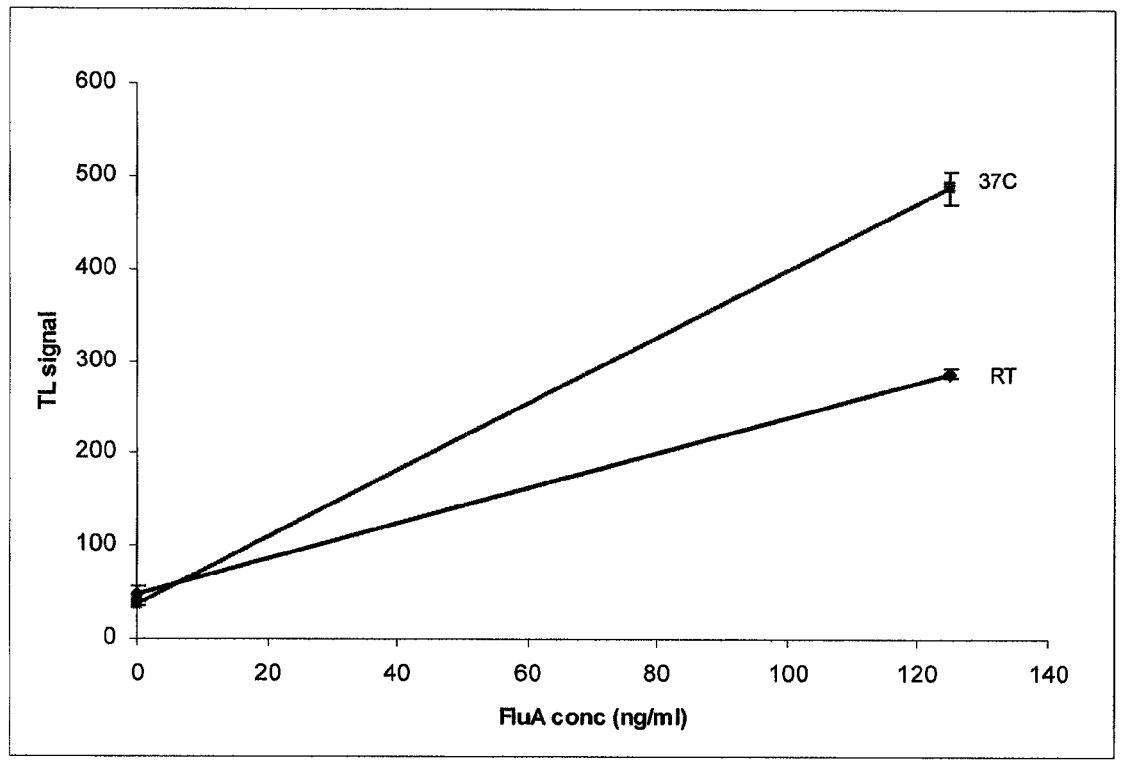
FIG. 1 depicts a comparison of signal for influenza detection particles at a sample capture zone (TL) of a lateral flow solid phase assay for ambient temperature (RT) and for elevated temperature (37 C), for various concentrations of influenza A analyte.

A description of example embodiments of the invention follows. The teachings of all patents, published applications and references cited herein are incorporated by reference in their entirety.

The present invention pertains to methods for decreasing non-specific binding in solid phase assays for the assessment of influenza; to methods for increasing specific binding in solid phase assays for influenza; and also to methods for reducing false-positive interactions in solid phase assays for influenza. The solid phase assays of the invention are lateral flow solid phase assays or capillary flow solid phase assays.

An assay, as used herein, refers to an in vitro procedure for analysis of a sample to determine the presence, absence, or quantity of influenza analyte(s) of interest. The methods of the invention utilize analyte binding agents that are members of a specific binding pair, in which a first member of the binding pair (the analyte—a type of influenza) reacts specifically with a second member (e.g., an analyte binding agent). Specific interaction between the members of the binding pair indicates that the first member of the binding pair preferentially binds or otherwise interacts with the second member of the binding pair, preferably to the exclusion of any binding to another compound in the assay. In one embodiment, the second member of the binding pair can be an antibody to the influenza analyte of interest. In this embodiment, the assay is an immunoassay.

The "influenza analyte(s) of interest," as used herein, refers to types of influenza (e.g., influenza A, influenza B, and influenza C), and can be an epitope, antigen or component of the influenza of interest. The influenza can be of any serotype. In the methods of the invention, one or more types of influenza can be investigated; each type is one of the analytes of interest.

In the methods of the invention, a test sample is assessed. The test sample can either be a sample which is suspected of containing influenza virus, or a test sample which is not suspected of containing influenza virus. In a preferred embodiment, the test sample is a mucosal sample (e.g., a nasal swab) or a nasal wash or aspirate sample. If desired, the test sample can be diluted; for example, it can be diluted with a solution (e.g., an aqueous solution or buffer).

The assays utilize influenza detection particles. The influenza detection particles are particles which can be coated with an influenza analyte binding agent (the second member of the binding pair) for an influenza analyte of interest. In a preferred embodiment, the influenza detection particles are liposomes, colloidal gold, organic polymer latex particles, inorganic fluorescent particles or phosphorescent particles. In a particularly preferred embodiment, the particles are polystyrene latex beads, and most particularly, polystyrene latex beads that have been prepared in the absence of surfactant, such as surfactant free Superactive Uniform Aldehyde/Sulfate Latexes (Invitrogen Corp., Carlsbad, Calif.). If there is one influenza analyte of interest, a single population of influenza detection particles can used; for example, the influenza detection particles are coated with one or more types of analyte binding agent for the influenza analyte of interest. Alternatively, either a single population of influenza detection particles, coated with at least one (one or more) type(s) of influenza analyte binding agent for the influenza analyte of interest, or more than one population of influenza detection particles, each population coated with one ore more types of influenza analyte binding agent for the influenza analyte of interest, can be used. If there is more than one influenza analyte of interest, either a single population of influenza detection particles, coated with one or more types of influenza analyte binding agent for each influenza analyte of interest, or more than one population of influenza detection particles, each population coated with one or more types of influenza analyte binding agent for one of the influenza analytes of interest, can be used. Representative influenza analyte binding agents include antibodies (or fragments thereof); haptens; drug conjugates; receptors; or other binding partners. In one preferred embodiment, the influenza analyte binding agent is an antibody to the influenza analyte of interest.

Antibodies can be monoclonal antibodies or polyclonal antibodies. The term "antibody", as used herein, also refers to antibody fragments which are sufficient to bind to the influenza analyte of interest. Alternatively, in another embodiment, molecules which specifically bind to the influenza analyte of interest, such as engineered proteins having influenza analyte binding sites, can also be used (Holliger, P. and H. R. Hoogenbloom, *Trends in Biotechnology* 13:7 9 (1995); Chamow, S. M. and A. Ashkenazi, *Trends in Biotechnology* 14:52 60:1996)).

The influenza detection particles must be sufficiently small to be transported along a membrane or through a capillary channel by capillary action of fluid, and also sufficiently small for a complex of influenza and influenza detection particles, as described below, to be transported by capillary action. The particles can be labeled to facilitate detection. The particles are labeled by a means which does not significantly affect the physical properties of the particles; for example, the particles are labeled internally (that is, the label is included within the particle, such as within the liposome or inside the polystyrene latex bead). Representative labels include luminescent labels; chemiluminescent labels; phosphorescent labels; enzyme-linked labels; chemical labels, such as electroactive agents (e.g., ferrocyanide); and colorimetric labels, such as dyes or fluorescent labels. In one embodiment, a fluorescent label is used. In another embodiment, phosphorescent particles are used, particularly "up-converting" phosphorescent particles, such as those described in U.S. Pat. No. 5,043,265.

The assays of the invention also utilize a solid phase apparatus. In one embodiment, the solid phase apparatus is a lateral flow solid phase apparatus. In the other embodiment, the solid phase apparatus is a capillary flow solid phase apparatus.

The lateral flow solid phase apparatus can be any solid phase apparatus designed for a lateral flow assay, such as the RAMP™ apparatus (Response Biomedical, Burnaby, British Columbia, Canada; see, e.g., apparatus described in U.S. Pat. Nos. 6,509,196; 7,175,992). Generally, the lateral flow solid phase apparatus includes a membrane through which the test sample will flow. The membrane can be made of a substance having the following characteristics: sufficient porosity to allow capillary action of fluid along its surface and through its interior; the ability to allow movement of coated particles (e.g., influenza detection particles as described herein) or complexes of particles and analyte of interest by capillary action (i.e., it must not block the particles or complexes of particles and analyte of interest); and the ability to be wet by the fluid containing the analyte (e.g., hydrophilicity for aqueous fluids, hydrophobicity for organic solvents). Hydrophobicity of a membrane can be altered to render the membrane hydrophilic for use with aqueous fluid, by processes such as those described in U.S. Pat. No. 4,340,482, or U.S. Pat. No. 4,618,533, which describe transformation of a hydrophobic surface into a hydrophilic surface. Examples of membrane substances include: cellulose, cellulose nitrate, cellulose acetate, glass fiber, nylon, polyelectrolyte ion exchange membrane, acrylic copolymer/nylon, and polyethersulfone. In a preferred embodiment, the membrane is made of cellulose nitrate (e.g., a cellulose nitrate membrane with a Mylar backing) The lateral flow solid phase apparatus can also optionally include other features, including sample pads, wicking pads, internal standard components, control components, or other features.

The capillary flow solid phase apparatus can be any solid phase apparatus designed for a capillary flow assay, such as the BioSite Triage® immunoassay products (BioSite Inc., San Diego, Calif.). Generally, the capillary flow solid phase apparatus includes a capillary channel through which the test sample will flow.

Whether a lateral flow solid phase apparatus or a capillary flow solid phase apparatus is used, the solid phase apparatus has an application point and one or more sample capture zones. The application point is the position on the membrane or in the capillary channel where the test sample can be applied. A sample capture zone refers to a point on the membrane or in the capillary channel at which at least one (one or more) sample capture reagent(s) is adsorbed (e.g., coated on and/or permeated through the membrane, or coated on the surface of the capillary channel). As used herein, the term "adsorbed" indicates that the agent is immobilized or adhered by non-covalent interactions, in contrast to covalent linkage where chemical means are used to generate an irreversible chemical bond of shared electrons between two linked molecules. Incremental movement (e.g., desorbtion) of an agent that is adsorbed onto a membrane or a surface of a capillary channel may occur, but will have negligible affect on the assays of the invention.

A sample capture reagent is an influenza analyte binding agent, such as those described above. A sample capture reagent need not be the same influenza analyte binding agent as described in relation to analyte binding agents on influenza detection particles, below; however, each sample capture reagent also forms a binding pair with its influenza analyte of interest, in that it specifically and preferentially binds to its influenza analyte of interest. In a preferred embodiment, a sample capture reagent is an antibody directed against an influenza analyte of interest; it can be directed against the same epitope of the influenza analyte as, or against a different epitope of the analyte from, the epitope that binds to the antibodies used as influenza analyte binding agents coated on the influenza detection particles. If there is more than one influenza analyte of interest, there will accordingly be more than one sample capture zone—one sample capture zone corresponding to each influenza analyte of interest (e.g., influenza A and influenza B). Each sample capture zone has at least one sample capture reagent adsorbed thereon, in which the sample capture reagent is an analyte binding agent for its particular (corresponding) influenza analyte of interest. More than one sample capture reagent can be present at each sample capture zone, if desired, provided that all of the sample capture reagents at a particular sample capture zone target the same influenza analyte of interest (although not necessarily the same epitope of that influenza analyte of interest). The distance between the sample capture zones can be varied; all that is required is that the distance is sufficient such that the zones do not overlap.

In one embodiment, the influenza detection particles can be positioned (e.g., dried or otherwise applied) onto the membrane of the lateral flow solid phase apparatus or the surface of the capillary flow solid phase apparatus (e.g., at or downstream from the application point). In this embodiment, they are attached to the solid phase apparatus in such a manner that upon application of fluid to the solid phase apparatus, they can be moved by capillary action of the fluid. In another embodiment, the influenza detection particles can be maintained in a separate sample collection apparatus that is utilized for collection of the test sample. Representative sample collection apparatus include a sample tube, a test tube, a vial, a pipette or pipette tip, or a syringe. If the influenza detection particles are contained within the sample collection apparatus are stored in a stable form within the sample collection apparatus. A "stable form," as the term is used herein, indicates a form in which the particles do not significantly change in chemical makeup or physical state during storage. The stable form can be a liquid, gel, or solid form. In preferred embodiments, the influenza detection particles contained within a sample collection apparatus are evaporatively dried; freeze-dried; and/or vacuum-dried.

To perform the assay, a test sample to be assessed for the presence of the influenza analyte(s) of interest, as described above, is used. If the influenza detection particles are on the solid phase apparatus, the test sample can be directly applied to the solid phase apparatus (e.g., at the application point); alternatively, it can be diluted or otherwise exposed to a buffer or other ingredients prior to application to the solid phase apparatus. In the embodiment in which the influenza detection particles are maintained in a separate sample collection apparatus, the test sample is introduced into (drawn into, poured into, or otherwise placed into) the sample collection apparatus. For example, in one embodiment, the test sample is drawn up into a sample collection apparatus that comprises a pipette tip. Introduction of the test sample into the sample collection apparatus results in mixing of the test sample with the influenza detection particles, so that the test sample now comprises the particles. If the influenza detection particles are evaporatively-, freeze- or vacuum-dried, the introduction of the test sample into the sample collection apparatus can result in rehydration and suspension of the influenza detection particles in the test sample. The test sample comprising rehydrated, suspended influenza detection particles is then applied to the solid phase apparatus. Regardless of whether the influenza detection particles are on the solid phase apparatus or in a separate sample collection apparatus, once the test sample comes into contact with the influenza detection particles, binding of influenza (if present) in the test sample to the influenza detection particles commences.

Once the test sample has been applied to the solid phase apparatus, the solid phase apparatus is then subjected to elevated heat. "Elevated" heat, as used herein, indicates that the temperature is at least about 5 degrees Celsius higher than ambient temperature (e.g., unheated or uncontrolled temperature, such as room temperature, which it typically approximately 21 degrees Celsius). In representative embodiments, the temperature is at least about 5 to 20 degrees Celsius higher than ambient temperature, such as at about between 35 to 40 degrees Celsius, inclusive (e.g., 37 degrees Celsius).

While the solid phase apparatus is being subjected to elevated heat, the lateral flow or capillary flow assay progresses. For example, if influenza is present in the test sample, continued binding occurs between the influenza and the influenza detection particles and continues as the assay progresses. "Binding" of influenza to influenza detection particles indicates that an influenza analyte binding agent coated onto the particle is interacting with (e.g., binding to) its influenza analyte of interest. Influenza detection particles may or may not have influenza analytes bound to the influenza analyte binding agent, depending on whether or not the influenza analyte of interest is present in the fluid sample and whether influenza analyte has bound to the influenza analyte binding agent on the influenza detection particles. Thus, a population of influenza detection particles may comprise particles having various amount of influenza analytes bound to the influenza analyte binding agents, as well as particles having no influenza analytes bound to the influenza analyte binding agents (just as the influenza detection particles initially have no influenza analyte bound to the influenza analyte binding agent).

Fluid moves by capillary action to and through the solid phase apparatus. Influenza detection particles, as well as influenza viruses if present in the test sample, move through the solid phase apparatus as a result of capillary action of the fluid, and the influenza detection particles move along the membrane (or along the capillary) to and through the sample capture zone(s). The movement of some of the influenza detection particles is arrested by binding of influenza detection particles to sample capture reagent(s) in the sample capture zone. Sample capture reagent binds to contacted influenza detection particles by binding to influenza which is bound to influenza analyte binding agent on the contacted influenza detection particles.

To assess the amount of influenza detection particles arrested in a sample capture zone, any appropriate means for the type of label used on the influenza detection particles can be used. For example, the amount can be detected by an optical method, such as by measuring the amount of fluorescence of the label of the influenza detection particles. Alternatively, the amount of particles can be detected using electrical conductivity or dielectric (capacitance). Alternatively, electrochemical detection of released electroactive agents, such as indium, bismuth, gallium or tellurium ions, as described by Hayes et al. (*Analytical Chem.* 66:1860-1865 (1994)) or ferrocyanide as suggested by Roberts and Durst (*Analytical Chem.* 67:482-491 (1995)) can be used. For example, if liposomes are used, ferrocyanide encapsulated within the liposome can be released by addition of a drop of detergent at the capture zone, and the released ferrocyanide detected electrochemically (Roberts and Durst, id.). If chelating agent-protein conjugates are used to chelate metal ions, addition of a drop of acid at the capture zone will release the ions and allow quantitation by anodic stripping voltametry (Hayes et al., id.).

The elevated temperature to which the solid phase apparatus is exposed results in a decrease of non-specific binding of influenza detection particles in the sample capture zone. "Non-specific binding," as used herein refers to the arrest of influenza detection particles in the sample capture zone due to binding of the influenza detection particles despite an absence of the influenza analyte. Non-specific binding is distinct from "background" binding, which occurs throughout the membrane (in lateral flow solid phase assays) or throughout the capillary tube (in capillary flow solid phase assays). Non-specific binding is in excess of the expected or measured background binding. A "decrease" in non-specific binding, as used herein, refers to an amount of non-specific binding that is significantly less than the amount of binding that would occur in the absence of elevated temperature. An amount is significantly less, for example, if the mean value for binding in the presence of elevated temperature is differs by at least 10% from the mean value for binding in the absence of elevated temperature. In other embodiments, there is a difference of at least one standard deviation between the mean value for binding in the presence of elevated temperature and the mean value for binding in the absence of elevated temperature.

Similarly, the elevated temperature to which the solid phase apparatus is exposed results in an increase of specific binding of influenza detection particles in the sample capture zone. "Specific binding," as used herein refers either to interaction between influenza analyte of interest with the influenza detection particles, or to the arrest of influenza detection particles in the sample capture zone due to binding of the influenza detection particles to the sample capture reagent, or to both. An "increase" in non-specific binding, as used herein, refers to an amount of specific binding that is significantly more than the amount of binding that would occur in the absence of elevated temperature. An amount is significantly more, for example, if the mean value for binding in the presence of elevated temperature is differs by at least 10% from the mean value for binding in the absence of elevated temperature. In other embodiments, there is a difference of at least one standard deviation between the mean value for binding in the presence of elevated temperature and the mean value for binding in the absence of elevated temperature.

In addition, the elevated temperature to which the solid phase apparatus is exposed eliminates false-positive interaction in assays of test samples containing little or no influenza analyte. As used herein, the term "false-positive" interaction is the capture and/or cessation of movement of particles in the sample capture zone that is unrelated to interaction or binding of the particles to the sample capture reagent in the sample capture zone. "False positive" interaction results in an amount of particles in the sample capture zone that is disproportionately and very high, compared to the actual amount of influenza virus present in the sample (e.g., in the case where influenza virus is not present in the sample). For example, samples the generate "false positive" interaction can be those that suffer from "matrix effects," in which the proteins and/or other components in the test sample cause increased arrest of particles in the sample capture zone due to various factors such as viscosity, weak positive cross-reactions of components in the test sample with the sample capture reagent, or other factors. Subjecting the solid phase apparatus to elevated heat reduces or eliminates such false positive interaction.

The methods of the invention enhance the sensitivity and specificity of lateral flow and capillary flow assays for influenza. Lower non-specific binding results in enhanced sensitivity in the assay, because it allows easier resolution of low concentrations of specific binding. Enhancement of specific binding similarly allows for easier resolution of low concentrations of specific binding, thereby enabling detection of the presence of smaller quantities of influenza analyte of interest in a test sample. Reduction of false positive interactions allows elimination of "up jumper" negative test samples from being considered positive for the influenza analyte of interest. The accuracy of test results is increased and enables more accurate treatment of disease.

The invention is now illustrated by the following Exemplification, which is not intended to be limiting in any way.

Exemplification: Reduction of Non-Specific Binding, Increase of Specific Binding, and Reduction of False-Positive Interaction in Influenza Assays A. Materials Lateral flow immunoassay solid phase apparatus was prepared using a nitrocellulose membrane, with 1.5 mg/ml, 1 ul/cm FluA antibody (sample capture reagent) striped at TL-position (sample capture zone), and 1 mg/ml, 1 ul/cm Goat anti-mouse antibody (control capture reagent) striped at ISL-position (control capture zone). The antibodies were striped on nitrocellulose membrane which was then blocked with 1% PVA, washed with 10 mM PB solution, and then dried and cut into 5 mm wide strips.

RAMP™ test cartridges were assembled using the strips, a sample pad, and a wicking pad.

Latex-antibody conjugate (influenza detection particles) were prepared as follows: 0.25 mg of FluA antibody (agent that binds to the influenza of interest, influenza A) (Fitzgerald Industries International, Inc., Concord, Mass., USA) and 1 ml of fluorescent dyed latex beads in 10 mM phosphate buffer (PB) solution were allowed to non-covalently adsorb by incubating at 2-8° C. for 12-18 hours. Cyanoborohydride in 1% Skim milk was added and incubated at 2-8° C. for 2-3 hours to form the covalent bonds of the latex-antibody conjugate and block non-specific binding. The latex-antibody conjugate was then washed several times using 10 mM PB solution to remove the cyanoborohydride and skim milk solution.

The latex-antibody conjugate was spotted in a pipette tip and dried using a vacuum pump to prepare RAMP™ assay tips (sample collection apparatus).

Sample Buffer was prepared using 138 mM PB, 138 mM NaCl, 3.6% BSA, 0.84% Surfactant 10 G, 0.6% casein, 0.05% Polyox, 0.05% v/v ProClin 300, pH 7.2.

B. Methods

A test sample was obtained with a nasal swab, and then was diluted by adding the sample directly into liquid sample buffer. The influenza detection particles were added to the prepared sample by mixing the sample using the pipette tip. The sample was then added into the RAMP™ test cartridge and cartridge was inserted in the RAMP™ Fluorescence Reader (Response Biomedical), which was modified to have a heating block, so that placing the cartridge over the heating block resulted in the temperature inside the cartridge of 37° C. The assay was incubated at 37° C. for the duration of the assay development time. After 14 minutes heated development time, the cartridge was scanned using the RAMP™ Fluorescence Reader. Fluorescence measurements were measured at the TL, ISL, and corresponding background positions of the strip. The TL and ISL signals were corrected by subtracting the corresponding background signals. Calculation of ratios for the FluA assays were performed by the reader as follows:

FluA Ratio=R10=TL/(TL+ISL)

For more than one analyte, a ratio is prepared using the sum of all lines, for example: Flu A ratio=TlA/(TLA+TLB+ISL)

Use of the ratio reduces the variability and increases the accuracy of the results, as compared to using only the TL signals due to inherent variability of the solid phase apparatus and sample-to-sample variability. These variabilities affect the TL and ISL signals similarly and thus the ratio value is used to reduce the variability in test results between multiple samples run.

C. Results

Increased Sensitivity (Increasing Specific Binding and Decreasing Non-Specific Binding): The experiment showed that when the influenza A assay was performed with heating to achieve an internal cartridge temperature of 37° C., the sensitivity of the assay for detection of influenza A antigen was increased compared to the same assay performed at Room Temperature (approx. 21° C.). The non-specific binding for the negative (0 ng/ml) sample decreased from TL signal of 49+/−8 F-units to 37+/−2 F-units, a 24% decrease with no overlap in error bars. The specific TL binding for the positive Flu A (125 ng/ml) sample increased from TL signal of 287+/−6 F-units to 488+/−18 F-units, a 70% increase with no overlap in error bars. This resulted in an increase of the TL Specific to Non-Specific (Sp:NonSp) from 5.9 to 13.1, a significant increase in sensitivity of the RAMP Flu A assay.

Figure 2:
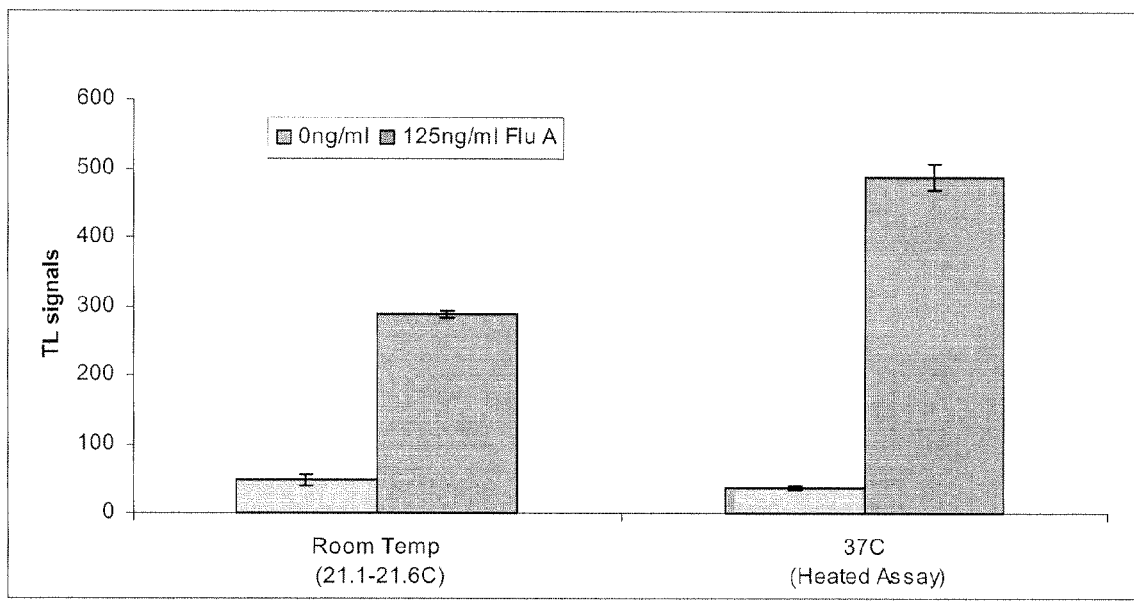
FIG. 2 is a bar graph depicting increased signal for influenza detection particles at a sample capture zone (TL) at elevated temperature, compared to ambient temperature.
Figure 3:
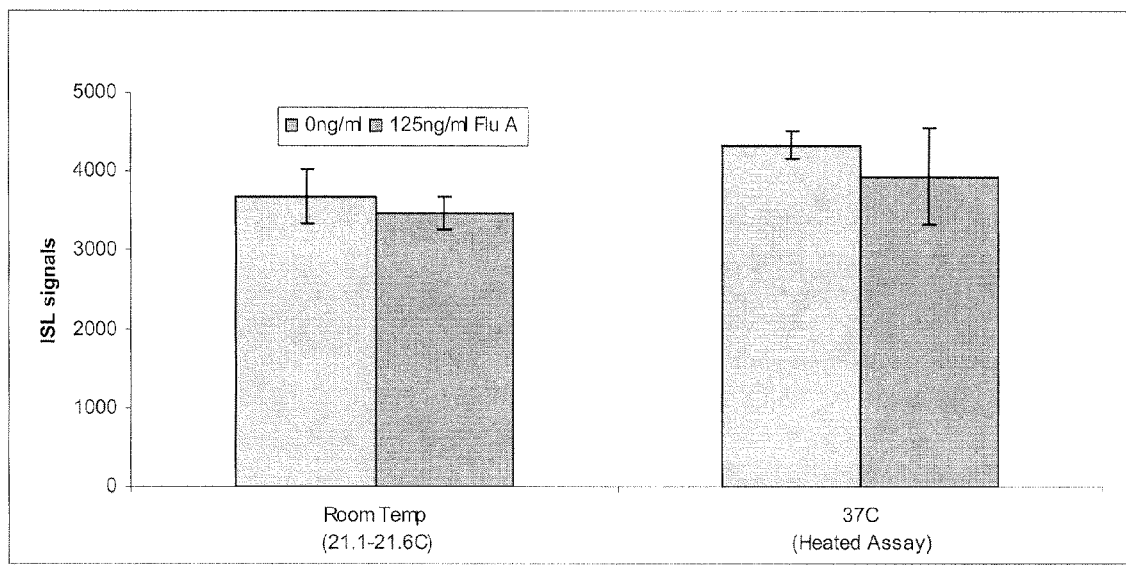
FIG. 3 is a bar graph depicting consistency of signal for influenza detection particles at a control capture zone (ISL) at both elevated temperature and ambient temperature.
Figure 4:
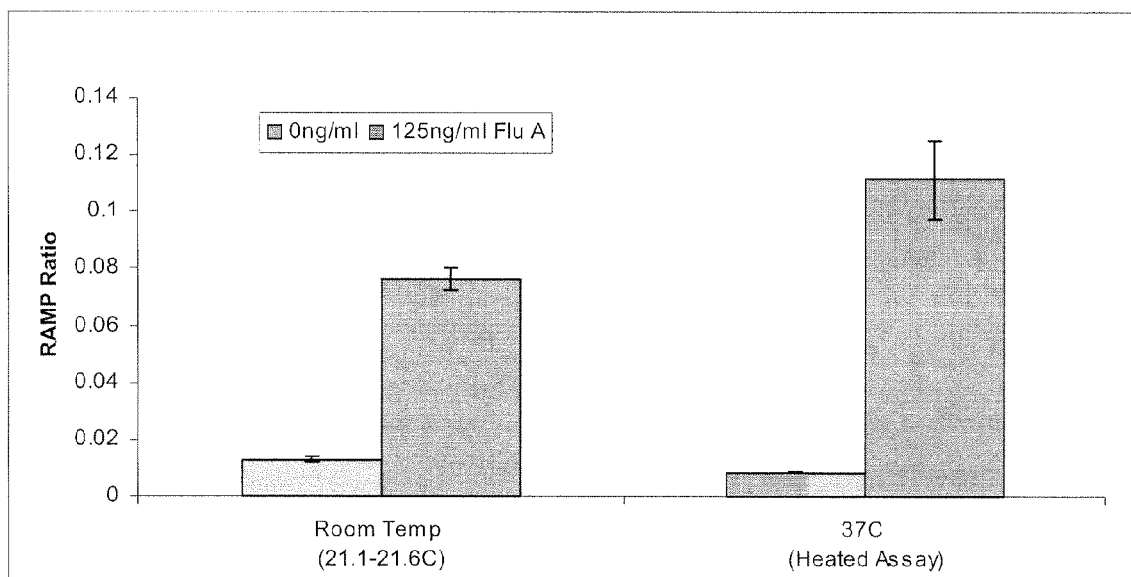
FIG. 4 depicts significantly enhanced ratios of influenza detection particles in a sample capture zone (TL) to total detected particles in both the sample capture zone and a control capture zone (TL+ISL), at elevated temperature compared to ambient temperature.

FIG. 1 demonstrates the increased sensitivity of the lateral flow solid phase assay for influenza A at an elevated temperature, compared to ambient temperature. The signal for influenza detection particles at a sample capture zone (TL) for ambient temperature (RT) and for elevated temperature (37 C), for influenza A analyte, demonstrates that elevated temperature consistently results in greater specific binding, yielding increased sensitivity in the assay. FIGS. 2 through 4 confirm this result, demonstrating that increased signal is present in the sample capture zone (TL) at elevated temperature compared to ambient temperature (FIG. 2) for a positive sample (increased specific binding), whereas decreased signal is present in the sample capture zone for a negative sample (degreased nonspecific binding). Signal remains similar at a control capture zone (ISL) at elevated temperature and at ambient temperature (FIG. 3), resulting in significantly enhanced ratios at elevated temperature compared to ambient temperature (FIG. 4).

Reduction of false-positive interaction: Nasal swab samples from a number of human in-house donor samples demonstrated high binding in the RAMP Flu A assay when performed at Room temperature (22° C.). These were from donors that were not infected with influenza A and thus should have had a negative RAMP Flu A test result. The high binding would have resulted in elevated RAMP Ratio values and have given a false positive Flu A result. When the same problem donor swab samples were tested in the RAMP Flu A assay performed with heating to achieve an internal cartridge temperature of 37° C., the false-positive binding at the TL was significantly reduced resulting in TL signals that gave a correct negative result for the sample. Thus, heating the RAMP Flu A assay resulted in correction of false-positive interaction in problem donor samples and reduces the risk of false positives in these samples.

TABLE 1

Results of assessment of specificity in heated vs. unheated influenza assays

Test Line (TL) signals

| Assay Temp | Sample (n = 3) | mean | sd | % cv | Sp:NSp | Sp-NSp |
|---|---|---|---|---|---|---|
| Room Temp (21.1-21.6 C.) | 0 ng/ml | 49 | 8 | 15.4 | — | — |
|  | 125 ng/ml Flu A | 287 | 6 | 2.0 | 5.9 | 225.4 |
| 37 C. (Heated Assay) | 0 ng/ml | 37 | 2 | 6.1 | — | — |
|  | 125 ng/ml Flu A | 488 | 18 | 3.7 | 13.1 | 430.7 |

Control Line (ISL) signals

| Assay Temp | Sample (n = 3) | mean | sd | % cv |
|---|---|---|---|---|
| Room Temp (21.1-21.6 C.) | 0 ng/ml | 3677 | 342 | 9.3 |
|  | 125 ng/ml Flu A | 3476 | 207 | 6.0 |
| 37 C. (Heated Assay) | 0 ng/ml | 4340 | 177 | 4.1 |
|  | 125 ng/ml Flu A | 3943 | 617 | 15.6 |

RAMP Ratio values

| Assay Temp | Sample (n = 3) | mean | sd | % cv | Sp:NSp | Sp-NSp |
|---|---|---|---|---|---|---|
| Room Temp (21.1-21.6 C.) | 0 ng/ml | 0.013 | 0.001 | 7.0 | — | — |
|  | 125 ng/ml Flu A | 0.077 | 0.004 | 5.0 | 5.9 | 0.1 |
| 37 C. (Heated Assay) | 0 ng/ml | 0.009 | 0.000 | 4.0 | — | — |
|  | 125 ng/ml Flu A | 0.111 | 0.014 | 12.4 | 13.1 | 0.1 |

TABLE 2

Results of assessment of reduction of false-positive interaction in heated vs. unheated influenza assays

| Donor Samples | Room Temp (22 C.) | 37 C. (Heated Assay) |
|---|---|---|
| Test Line (TL) signals | | |
| M5 | 181 | 37 |
| M35 | 1445 | 67 |
| F93 | 287 | 62 |
| M103 | 701 | 90 |
| M134 | 173 | 30 |
| Control Line (ISL) signals | | |
| M5 | 5160 | 7135 |
| M35 | 3547 | 5669 |
| F93 | 5009 | 6915 |
| M103 | 5480 | 6696 |
| M134 | 6996 | 8183 |
| RAMP Ratio values | | |
| M5 | 0.034 | 0.005 |
| M35 | 0.289 | 0.012 |
| F93 | 0.054 | 0.009 |
| M103 | 0.113 | 0.013 |
| M134 | 0.024 | 0.004 |

Figure 5:
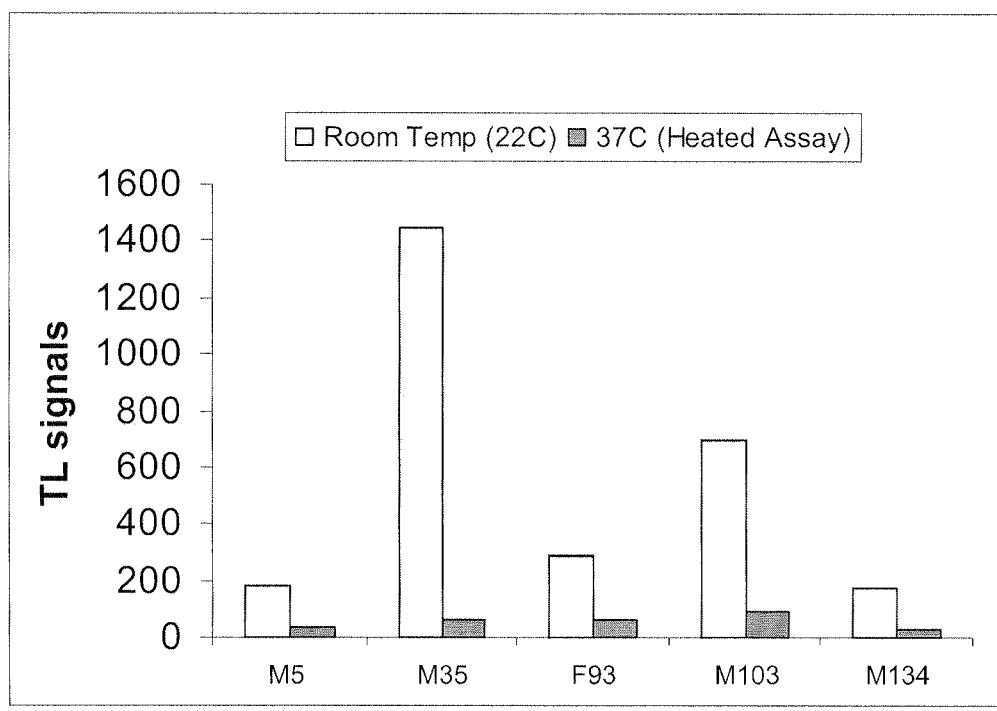
FIG. 5 is a bar graph depicting decreased signal for influenza detection particles at a sample capture zone (TL) at elevated temperature, compared to ambient temperature.
Figure 6:
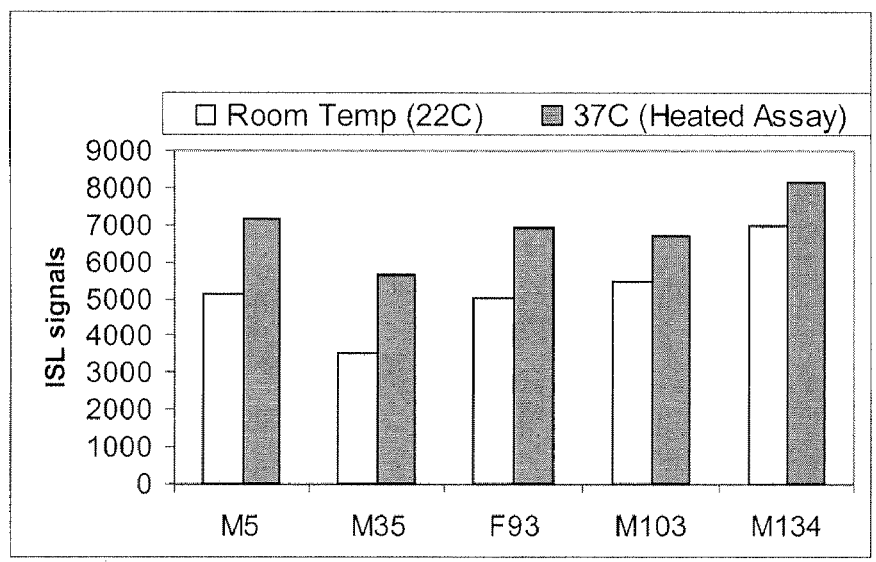
FIG. 6 is a bar graph depicting increase of signal for influenza detection particles at a control capture zone (ISL) at elevated temperature, compared to ambient temperature.
Figure 7:
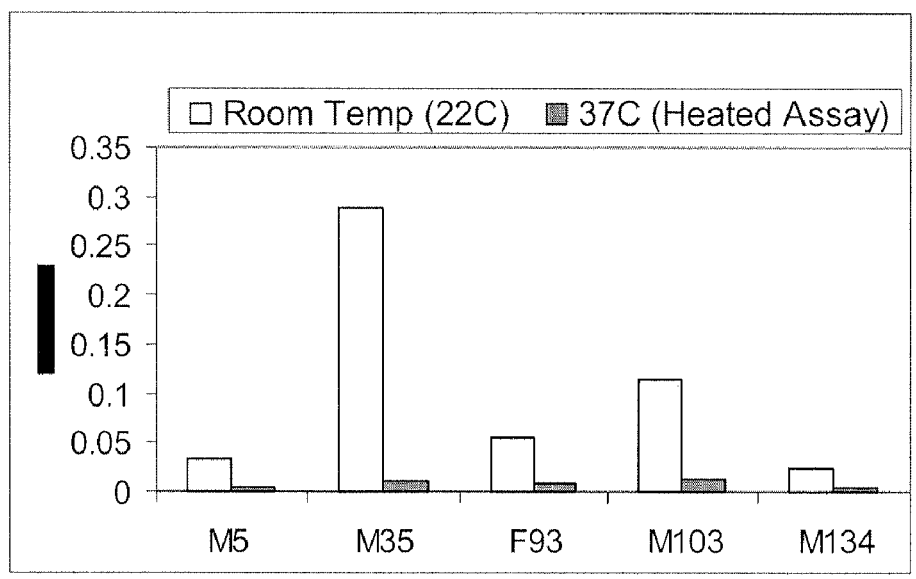
FIG. 7 depicts ratios of influenza detection particles in a sample capture zone (TL) to total detected particles in both the sample capture zone and a control capture zone (TL+ISL), at elevated temperature compared to ambient temperature, demonstrating elimination of false-positive interaction at elevated temperature compared to ambient temperature.

FIGS. 5 through 7 demonstrate that decreased signal is present in the sample capture zone (TL) at elevated temperature compared to ambient temperature (FIG. 5), whereas increased signal occurs at a control capture zone (ISL) at elevated temperature compared to ambient temperature (FIG. 6), resulting in ratios that indicate elimination of false-positive interaction at elevated temperature compared to ambient temperature (FIG. 7). It is noted that the increase in ISL in FIG. 6 is a side effect of decreased TL binding.

While this invention has been particularly shown and described with references to example embodiments thereof, it will be understood by those skilled in the art that various changes in form and details may be made therein without departing from the scope of the invention encompassed by the appended claims.

What is claimed is:

1. A method for decreasing non-specific binding of influenza detection particles on a solid phase apparatus in an assay for influenza, the method comprising subjecting a solid phase apparatus having influenza detection particles applied thereon to an elevated temperature subsequent to application of a test sample to the solid phase apparatus, whereby the non-specific binding of the influenza detection particles on the solid phase apparatus is decreased.

2. The method of claim 1, wherein the influenza is selected from the group consisting of: influenza A and influenza B.

3. The method of claim 1, wherein the solid phase apparatus comprises an application point and at least one sample capture zone having at least one sample capture reagent immobilized thereon.

4. The method of claim 3, wherein the influenza detection particles are applied at the application point and, upon subsequent application of the test sample, are moved by capillary action through the solid phase apparatus to and through the sample capture zone, and wherein influenza detection particles may bind to a sample capture reagent.

5. The method of claim 3, wherein the test sample comprises the influenza detection particles, and wherein the application of the test sample to the solid phase apparatus applies the influenza detection particles to the solid phase apparatus and results in movement of the influenza detection particles through the solid phase apparatus by capillary action to and through the sample capture zone, and wherein influenza detection particles may bind to a sample capture reagent.

6. The method of claim 3, wherein the solid phase apparatus is a lateral flow solid phase apparatus.

7. The method of claim 3, wherein the solid phase apparatus is a capillary flow solid phase apparatus.

8. The method of claim 1, wherein the elevated temperature is about 5 to 20 degrees Celsius above ambient temperature.

9. A method for increasing specific binding of influenza detection particles on a solid phase apparatus in an assay for influenza, the method comprising subjecting a solid phase apparatus having influenza detection particles applied thereon to an elevated temperature subsequent to application of a test sample to the solid phase apparatus, whereby the specific binding of influenza detection particles on the solid phase apparatus is increased.

10. The method of claim 9, wherein the influenza is selected from the group consisting of: influenza A and influenza B.

11. The method of claim 9, wherein the solid phase apparatus comprises an application point and at least one sample capture zone having at least one sample capture reagent immobilized thereon.

12. The method of claim 11, wherein the influenza detection particles are applied at the application point and, upon subsequent application of the test sample, are moved by capillary action through the solid phase apparatus to and through the sample capture zone, and wherein influenza detection particles may bind to a sample capture reagent.

13. The method of claim 11, wherein the test sample comprises the influenza detection particles, and wherein the application of the test sample to the solid phase apparatus applies the influenza detection particles to the solid phase apparatus and results in movement of the influenza detection particles through the solid phase apparatus by capillary action to and through the sample capture zone, and wherein influenza detection particles may bind to a sample capture reagent.

14. The method of claim 11, wherein the solid phase apparatus is a lateral flow solid phase apparatus.

15. The method of claim 11, wherein the solid phase apparatus is a capillary flow solid phase apparatus.

16. The method of claim 9, wherein the elevated temperature is about 5 to 20 degrees Celsius above ambient temperature.

* * * * *